United States Patent [19]

Sanderson

[11] Patent Number: 4,478,823

[45] Date of Patent: Oct. 23, 1984

[54] IMMUNOLOGICAL PREPARATIONS CONTAINING PURIFIED MHC ANTIGENS BONDED TO OTHER ANTIGENS

[75] Inventor: Arnold R. Sanderson, East Grinstead, England

[73] Assignee: National Research Development Corporation, London, England

[21] Appl. No.: 456,976

[22] Filed: Jan. 10, 1983

Related U.S. Application Data

[63] Continuation of Ser. No. 116,677, filed as PCT GB78/00016, Sep. 27, 1978, published as WO79/00160, Apr. 5, 1979 § 102(e) date May 29, 1979, abandoned.

[30] Foreign Application Priority Data

Sep. 28, 1977 [GB] United Kingdom ............... 40339/77

[51] Int. Cl.$^3$ .................... A61K 39/385; A61K 39/00; C07G 7/00
[52] U.S. Cl. ................................. 424/88; 260/112 R; 260/112 B; 424/85; 424/86; 424/87; 424/89; 424/91; 424/92; 436/543
[58] Field of Search ....................... 260/112 R, 112 B; 424/88, 89.91, 92

[56] References Cited

U.S. PATENT DOCUMENTS

| 4,185,090 | 1/1980 | McIntire | 424/88 X |
| 4,372,945 | 2/1983 | Likhite | 424/92 |
| 4,400,376 | 8/1983 | Sanderson | 260/112 R X |

FOREIGN PATENT DOCUMENTS

1945251 11/1971 Fed. Rep. of Germany.

OTHER PUBLICATIONS

Gooding et al. J. of Experimental Med., 1974, 140, 61–77.
Henning et al. Nature, vol. 263, 1976, pp. 689–691.
Garrido et. al. Nature, vol. 261, 1976, pp. 705–707.
Fujimoto et. al. Journal of Immunology, 1973, 111, 1093–1100.
Sanderson et. al. Transplantation, vol. 16, No. 4, (1973), 304–312.
Sanderson, Nature, vol. 269, 1977, pp. 414–417.

*Primary Examiner*—Howard E. Schain
*Attorney, Agent, or Firm*—Oblon, Fisher, Spivak, McClelland & Maier

[57] ABSTRACT

An immunologically active preparation for human or veterinary use comprises an antigenic material in combination with an MHC antigen.

49 Claims, No Drawings

IMMUNOLOGICAL PREPARATIONS CONTAINING PURIFIED MHC ANTIGENS BONDED TO OTHER ANTIGENS

This is a continuation of application Ser. No. 116,677, filed as PCT GB 78/00016, Sep. 27, 1978, published as WO 79/00160, Apr. 5, 1979 § 102(e) date May 29, 1979, now abandoned.

This invention relates to immunological preparations, particularly those containing antigenic materials.

Immunisation against infectious diseases is widely used in both a human and a veterinary context. It is often the case, however, that the antigenic material contained in the immunological preparation is not as immunogenic as could be desired, necessitating the use of a plurality of injections of the preparation. As an alternative, or in addition to the use of repeated injections, as adjuvant may be incorporated in the immunological preparation in order to increase the immune response provoked by the antigenic material. However, the effective adjuvants at present available, for example Freund's incomplete and complete adjuvants, have disadvantages particularly for human use. For some time, therefore, attempts have been made to discover new forms of adjuvant which would simplify immunization procedures and reduce the amounts of antigenic material required or amplify the response to a given quantity of antigenic material. Such an effect is applicable not only for protective immunization but also for the production of therapeutic or diagnostic immunological and serological reagents.

It has now been found that members of a group of naturally occuring substances have the effect of increasing the immunogenicity of antigenic materials when administered in combination therewith.

Accordingly, the present invention comprises an immunologically active preparation comprising an antigenic material in combination with a MHC (Major Histocompatability Complex) antigen.

MHC antigens have been found in all animal species (including man) where they have been sought, being carried on the surface of nucleated cells of tissues, and constitute a particularly polymorphic systems within any species. Therefore, although it is necessary in order for the MHC antigen to enhance the immunogenicity of the antigen material with which it is combined, that the MHC antigen should contain an antigenic determinant or determinants foreign to the recipient, the extreme polymorphism of these MHC antigens is generally sufficient to ensure that this is the case between one member of a species and another, except in the extreme case of members of a species which are genetically identical. The MHC antigen may therefore be from either the same species or another species, for example a phylogenetically similar species such as a primate in the case of preparations for human administration. MHC antigen from the same species may often be preferred, however, unless there are reasons, particularly an enhancement of effect, for using MHC antigen from another species.

MHC antigens of particular interest in the context of the present invention are the HLA (Human Lymphocyte Antigen) antigens in man and the analagous antigens of other species. Such MHC antigens are referred to by many workers as SD (Serologically Determined) antigens and may be distinguished from other types of MHC antigen such as the Ia antigens of mice and their equivalents in man (DRW) and other animal species. Examples of the MHC antigens analagous to HLA in other species are RLA in rabbits and H-2 in mice, etc.

The MHC antigens may be of various specificities. Moreover they may be of the naturally occuring form or of derivatives therefrom which retain the epitope intact, for example papain-solubilised MHC antigens.

The present invention is widely applicable to a whole variety of antigenic materials which are of use in vaccines. The term antigenic material as used herein thus covers any substance that will elicit a specific immune response when administered in combination with a MHC antigen and includes antigenic determinants such as peptides (small or large), oligo or polysaccharides, alloepitopes, haptens and the like.

In the context of vaccines for human administration, a variety of microbial antigens may be used as the antigenic material. Examples include bacterial antigens, for instance toxins such as *Staphylococcus enterotoxin* and particularly toxoids such as diphtheria and tetanus toxoid, and viral antigens such as those derived from the influenza and the rabies viruses. The invention is also of interest, however, in relation to vaccines against other forms of pathogen such as protozoa and fungi and also in relation to the field of contraception, for example for vaccination against HCG when a hormone peptide is used as the antigenic material, as well as in the immunotherapy of cancer. The invention is also of considerable interest and of similar wide applicability in the context of veterinary vaccines for both mammalian and avian administration, for example in the treatment of the viral foot and mouth disease in cattle and pigs. For the treatment of cattle and pigs bovine LA and porcine LA are preferred as the MHC antigen. As indicated above, however, there may be an advantage in using the MHC antigen of a closely related species so that the use of bovine LA in pigs and of porcine LA in cattle may be considered in addition to the more usual intraspecies usage.

MHC antigens may be readily obtained from natural sources and procedures for doing this are described in the literature. The HLA antigens, for example, may conveniently be obtained by extraction of the membranes of human lymphoblastoid cells cultured in a suitable medium to provide sufficient quantities thereof for extraction. Alternatively, a human non-lymphoid cell line may be used as the source. In their natural form MHC antigens are generally bound to a protein molecule, for example HLA and the equivalent MHC antigens of other species being bound to B2-microglobulin (B2M). The nature of the binding between the two molecules is not yet known for any species, although present indications are that it is not of the form of a covalent bond. However, the bonding is strong enough so that in several species including man B2M is co-isolated with MHC antigen under normal circumstances. It is not necessary to remove the B2M molecule from the MHC molecule before the latter is used in the present invention and indeed it is preferred to use the MHC antigen in the form of a complex with the appropriate B2M.

Accordingly the present invention excludes known naturally occurring combinations consisting of a MHC antigen with a B2M or like protein as the only immunologically active species, but particularly includes such combinations, for example a MHC-B2M complex, when combined with a further antigenic material.

The bonding between the MHC antigen and the antigenic material may be of a variety of types including bonds of a noncovalent type such as hydrogen bonds, ionic bonds, and hydrophobic bonds, as well as covalent bonds. The preparation of the MHC antigen-antigenic material combination may require varying degrees of manipulation ranging from simple mixing of the two components to the deliberate construction of a covalent bond between the MHC antigen and the antigenic material used. It will be appreciated that when, as is usually the case, the antigenic material is combined with a MHC-B2M complex, then the material may be attached through either the B2M component or a suitable modification thereof (such modifications being included by such terms as MHC-B2M complex and B2M protein etc. when used herein in a general sense), or the MHC epitope bearing protein. Methods of effecting combination include various of the techniques described in the literature for attaching antigens or haptens to proteins, for example the use of a coupling agent such as chromic chloride, divinyl sulphone, cyanogen bromide, bis-diazotised benzidine (BDB) and especially glutaraldehyde, tannic acid and carbodiimides, for example 1-ethyl-3-(3-dimethylaminopropyl)carbodiimide hydrochloride (EDC).

One particularly convenient approach which is based upon a procedure described, for example, by Kitagawa and Aikawa in the Journal of Biochemistry, 1976, 79, 233, involves the use of a heterobifunctional coupler. Such a coupler contains a group which will bond to the antigenic material and a different group which will bond to the MHC antigen or MHC-B2M complex. Conveniently, the antigenic material is attached through the B2M portion of the complex and a preferred approach comprises the addition of the coupler to the B2M protein followed by exchange of the modified B2M protein with the B2M protein in the naturally occurring MHC-B2M complex and the addition of the desired antigenic material to the complex through the free end of the coupler.

One example of such a heterobifunctional coupler which has been used with some success is m-maleimidobenzoyl N-hydroxysuccinimide ester (MBS). This coupler will couple with free amino groups through active ester acylation by the m-maleimidobenzoyl groups and also with sulphydryl groups, for example of cysteine, by addition at the double bond of the maleimido group. For the sake of simplicity the symbol MBS has also been used hereinafter in identifying products linked through the use of this reagent although such products will, of course, only contain a residue of the reagent. By blocking sulphydryl groups in the MHC antigen, for example by the use of N-ethyl maleimide, linking to the MHC-B2M couplex is effected through free amino groups only (the B2M protein containing no sulphydryl groups) and coupling of the antigenic material may then be effected through the sulphydryl groups which are naturally present therein or are inserted for this purpose.

The amounts of antigenic material incorporated as the immunologically effective agent to provide pharmaceutical preparations according to the present invention may be similar to those used in existing vaccines incorporating such material, but it may be possible in view of the increased immunogenicity to reduce these amounts. Similarly, although additional adjuvants may be incorporated into the preparations, this may likewise be unnecessary. The proportion of MHC antigen to antigenic material may be varied according to the particular circumstances. However, as a guide it may be indicated that in primates three dosages containing about 10, 10 and 5 micrograms of HLA have proved effective and that broadly similar unit dosage levels are generally applicable in humans, for example in the range from 5 to 100 micrograms, particularly from 10 to 50 microgram, for example about 25 micrograms. A similar basis may be used for veterinary applications with due consideration for variation in body weight.

In other respects, the preparations may be formulated in a similar manner to conventional vaccines, for example in a medium such as isotonic saline, and may be administered similarly, often by a parenteral route, for example intravenously, intramuscularly or subcutaneously.

The present invention thus includes a method for the immunization of a mammal or a bird which comprises administering thereto as an immunologically effective agent an antigenic material which is in combination with an MHC antigen.

The invention is illustrated by the following examples. Also provided are the details of an experiment illustrating the ability of MHC antigens to enhance the immunogenic effect of antigenic materials by reference to the immunogenicity of B2M in an HLA-B2M combination (such a known combination, however, being excluded from the scope of the invention).

EXPERIMENT

Comparison of Immunogenicity of Free and HLA Antigen B2-Microglobulin (1) Isolation of materials.

Papain-solubilized HLA antigens (in combination with B2M) were prepared from typed cadaver human spleen as described by Sanderson and Welsh in Transplantation, Volume 16, 304–312, (1973), or from cultured human cell lines as described by Turner, Cresswell, Parham, Strominger, Mann, and Sanderson, Journal of Biological Chemistry, Volume 250, 4512–4518, (1975). In this procedure cells were disrupted by freeze-thawing, and membranes prepared by differential centrifugation and washing. HLA-antigen was solubilized by papain, and purified by DEAE chromatography, CM chromatography, and Sephadex filtration. Assessment of the degree of purification was made at each stage by a standard assay involving the inhibition of cytolosis of $^{51}$chromium-labelled human peripheral lymphocytes by specific HLA antibodies and complement.

Human B2M protein was isolated according to the method of Berggard and Bearn, Journal of Biological Chemistry, Volume 243, 4095–4100 (1968).

(2) In vivo Tests

Two groups of *Macaca irus* primates were treated by intramuscular administration with (a) 50-100 μg doses of the free B2M protein in incomplete Freund's adjuvant, and (b) 0.5 to 1.0 μg doses of the papain-solubilised HLA-B2M complex (protein content based on an assumed final purity of 10% validated by radio immunoassay of B2M content), respectively. In the former instance six booster injections were required to produce a detectable response and in the latter case though six booster injections were given, a detectable response was present after two of these had been given.

Anti-B2M titres were determined as follows. 5 μl of $^{125}$I-B2M solution was added to 8 μl volumes of five fold dilutions of the animal's serum in diluent, followed by incubation at room temperature for 1 hour, then the addition of 0.180 ml of 19% Na$_2$So$_4$ solution and further incubation at room temperature for 1 hour. After centrifugation at 1,000 g for 5 minutes, 50% of the supernatant was sampled and the results were plotted as the percentage radionuclide remaining in solution against antiserum dilution in the reaction volume. The titre of antiserum was the dilution at which 50% of the nuclide was precipitated. Control samples containing diluent in place of antiserum were run and the results were corrected according to the titration value given by a reference chicken anti-human B2M serum.

The results obtained for anti-B2M titre and other tests are shown in Table 1 below.

TABLE 1

| Injected Protein | Anti-B2M titre | | Human Lymophocytotoxin: 50% cytotoxic | |
|---|---|---|---|---|
| | 3 boosts | 6 boosts | Titre (1) | SR[2] |
| 50–100 μg Free B2M | nil | 93 ± 13 | 8 ± 2 | 1.0 |
| 0.5–1.0 μg Papain-solubilised HLA Antigens | 1100 ± 275 | 2,406 ± 1295 | 3250 ± 1673 | 4.8 ± 1.1 |

(1) Estimated in microtitre plates using 25 μl volumes of lymphocytes, antiserum dilutions, and rabbit complement, and a Trypan blue indication of cell death.

(2) Specificity Ratio: the ratio of titre with cells positive or negative for a HLA specificity, based on analysis of a population of 20 cell types covering the relevant specificities.

EXAMPLES (Products are isolated in solid form by freeze drying. As an alternative, for storage their solutions may be frozen at −20° C.).

EXAMPLE 1

Preparation of Dinitrophenyl-B2M-HLA (1) Human B2M prepared as described in the Experiment is reacted with fluorodinitrobenzene essentially by the general procedure for the introduction of dinitrophenyl (DNP) groups which is described by Hudson and Hay in Practical Immunology (Blackwell) Scientific Publications, London, 1976). A low level of 3H labelled fluorodinitrobenzene is incorporated into the bulk of unlabelled fluorodinitrobenzene to provide a convenient means of identifying the complex. The DNP-B2M complex is purified by gel filtration chromatography on G25 Sephadex using 0.05M tris chloride buffer (tris is an abbreviation for tris-hydroxymethylamino methane) of pH 7.3, a yield of about 50% typically being obtained of a complex containing 1 to 2 DNP residues per protein molecule.

(2) Papain solubilised HLA [4 nm; in combination with B2M- prepared as described in Experiment] is incubated with DNP-B2M complex [54 nm; prepared as described in (1) above] in a total volume of 0.65 ml phosphate buffered saline for 16–20 hours. The reaction mixture is purified by gel filtration on G75 Sephadex using 0.05M tris chloride buffer of pH 7.3, typically giving a near quantitative yield of DNP-B2M-HLA.

EXAMPLE 2

Immunization Experiments with Dinitrophenyl-B2M-HLA

*Macaca irus* primates are immunized intramuscularly with 10 to 50 microgram quantities of the dinitrophenyl hapten coupled to B2M-HLA (prepared as described in Example 1) or coupled to ovalbumin to provide a control, ovalbumin being of comparable size to B2M-HLA; the DNP-ovalbumin containing 1–2 DNP residues per protein molecule is prepared by an analagous procedure to that described in Example 1 (1) for DNP-B2M. The hapten is administered in incomplete Freund's adjuvant and booster injections are given at 2 to 3 week intervals, bleeds being taken before and during the immunization protocol.

For the assessment of immunity in each case the hapten is attached to the wells of a soft plastic plate (Cooke Microtitre Plate) by incubation for 1 hour at 37° C. of 0.05 ml of a solution containing 0.02 mg/ml of protein in phosphate buffered saline. After washing, 0.025 ml dilutions of serum are incubated in each well for 1 hour at 37° C. After further washing, the wells are each incubated with 0.01 ml $^{125}$I-labelled F(ab)$_2$ fragments of immunopurified goat anti human F(ab)$_2$. The wells are then counted in a well type gamma spectrometer, appropriate controls being included. Association of nuclide with a well indicates the presence of the radio labelled anti F(ab)$_2$ protein and thus of primate antibodies which cross react with human immunoglobulins and are detected by the goat reagent. Positive and negative controls typically differ by at least a factor of 3 to 4 fold and typical titres are shown in Table 2 below.

TABLE 2

| Antigenic material | Titre | |
|---|---|---|
| | after boost 1 | after boost 2 |
| DNP-ovalbumin | nil | nil |
| DNP-B2M-HLA | 32 | >128 |

EXAMPLE 3

Preparation of Fab-B2M-HLA (1) Human B2M [8.3 mg, 714 nm; prepared as described in the Experiment] is incubated in 1.0 ml of 0.05M tris chloride of pH 7.3 with m-maleimidobenzoyl N-hydroxysuccinimide ester (MBS) for 1.5 hours at room temperature. The acylation reaction is terminated by the addition of excess lysine (0.05 ml of a 20 mg/ml aqueous solution of lysine) and the m-maleimidobenzoyl derivative of B2M (MBS-B2M) is separated from low molecular weight contaminants by gel filtration on Sephadex G50 using 0.05M tris chloride of pH 7.3 as eluant. Emergence of the protein peak is accompanied simultaneously by the SH coupling capacity as determined by reaction with cysteine resulting in an increase in the Ellman calorimetric assay for SH groups. The MBS-lysine emerges from the column much later than the MBS-B2M and is detected by the Ellman test. The fractions containing B2M-MBS are pooled and lyophilised, this procedure resulting in a negligible deterioration of the SH coupling capacity.

(2) Papain solubilised HLA [0.125 mg, 2.8 nm; in combination with B2M- prepared as in the Experiment and treated with 0.01M N-ethylmaleimide for 1 hour at room temperature, followed by reisolation by gel filtration, to block reactive SH groups] is reacted with MBS- B2M [0.83 mg, 62 nM prepared as in (1) above] in phosphate buffered saline for 1 hour and the reaction is purified by gel filtration chromatography on G75 Sephadex using 0.05M tris chloride buffer of pH 7.3 to give MBS-B2M-HLA, typically in quantitative or near quantitative yield.

(3) MB 4-B2M-HLA [the whole of the product of (2) above] is reacted with human Fab (11.6 mg; 232 nm) in 0.1 ml of 0.15M tris chloride for 5 hours at room temperature. The products are then separated by chromatography on Sephadex G200 using 0.05M tris chloride of pH 7.3 as eluant. The Fab-MBS-B2M-HLA product emerges from the column at a position corresponding to a molecular weight of about 90,000–100,000 and is established to contain B2M and Fab by radio immunoassay, and also to be specifically inhibitory for HLA antisera. The yield as determined by specific inhibitory capacity with HLA alloantisera typically corresponds to a recovery of about 50% of the total HLA antigen activity. The remainder of the activity corresponds to a product emerging in the anticipated position for unreacted MBS-B2M-HLA as established using radioiodinated HLA alloantigen.

EXAMPLE 4

Preparation of HCG-B2M-HLA

MBS-B2M-HLA is prepared as described in Example 3(2) above using the same quantities of reactants. The whole of the product obtained is reacted with HCG (0.075 mg; 20.8 nM) in 0.1 ml of 0.05M tris chloride buffer of pH 7.3 for 3 hours at room temperature. The products are separated by G75 Sephadex chromatography using 0.005M tris chloride buffer of pH 7.3. The HCG-MBS-B2M-HLA is eluted from the column just ahead of the position expected for HLA protein on this column, typically being obtained in 1 to 2% yield. The low yield obtained as compared with that of Example 2(3) is believed to be due to the smaller amount of the antigenic material used in this instance, the reaction yield based upon HLA being very much higher when a greater excess of the antigenic material is used.

EXAMPLE 5

Preparation of B2M-HLA Linked Influenza Neuraminidase and Haemagglutinin

MBS-B2M-HLA is prepared as described in Example 3(2) above using the same quantities of reactants. A suspension (5 ml) of a mixture of influenza virus neuraminidase and haemagglutinin (Strain A/Victoria/3/75; 5,222 IU/0.5 ml: Lowry protein 1 mg/ml; neuraminidase 5650 U/ml; supplied by Evans Medical Ltd.) is freeze dried and the product reconstituted in 0.2 ml of water. To the aqueous neuraminidase/haemagglutinin is added the MBS-B2M-HLA and the mixture is kept overnight at room temperature. The resulting neuraminidase/haemagglutinin-MBS-B2M-HLA is used is crude form or isolated by gel filtration chromatography in a similar fashion to the products of Examples 3(3) and 4.

EXAMPLE 6

Preparation of B2M-HLA Linked *Staphylococcus Enterotoxin B*

MBS-B2M-HLA is prepared as described in Example 3(2) above using the same quantities of reactants. *Staphylococcus enterotoxin B* (10 mg) obtained in solid form by freeze drying is reconstituted in 0.25 ml water. To the aqueous enterotoxin is added the MBS-B2M-HLA and the mixture is kept overnight at room temperature. The resulting enterotoxin-MBS-B2M-HLA is used in crude form (after extensive dilution) or is isolated by gel filtration chromatography in a similar fashion to the products of Examples 3(3) and 4.

EXAMPLE 7

Immunization Experiments with B2M-HLA Linked *Staphylococcus Enterotoxin B*

*Macaca irus* primates are immunized intramuscularly with about 1 to 5 microgram quantities of antigen or antigen linked to B2M-HLA (prepared as described in Example 6) in incomplete Freund's adjuvant. Three closely spaced injections are given and the primates are then bled and the serum evaluated.

For the assessment of immunity in each case the *S. enterotoxin* is attached to the *wells* of a soft plastic plate (Cooke Microtitre Plate) by incubation for 1 hour at 37° C. of 0.05 ml of a solution containing 0.01 mg/ml of protein in phosphate buffered saline. After washing, 0.025 ml dilutions of serum are incubated in each wall for 1 hour at 37° C. After further washing, the wells are each incubated with 0.01 ml $^{125}$I-labelled F(ab)$_2$ fragments of immunopurified goat anti human F(ab)$_2$. The wells are then counted in a well type gamma spectrometer, appropriate controls being included. Association of nuclide with a well indicates the presence of the radio labelled anti F(ab)$_2$ protein and thus of primate antibodies, which cross-react with human immunoglobulins and are detected by the goat reagent. Negative controls typically differ by at least a factor of 3 to 4 fold and typical titres are shown in Table 3 below.

TABLE 3

| Antigenic material | Titre |
|---|---|
| S. enterotoxin | nil |
| S. enterotoxin-B2M-HLA | >128 |

The following claims are subject to the proviso that no claim is made relating to the combination of an MHC antigen with a protein with which it occurs naturally as the only immunologically active species in the combination.

I claim:

1. A synthetic immunogenic complex comprising a purified MHC antigen bonded to a second antigen, with the provisos that said second antigen is not a protein with which said MHC antigen is normally associated in nature and is not another MHC antigen.

2. The immunogenic complex according to claim 1, wherein the second antigen is a viral antigen.

3. The immunogenic complex according to claim 2, wherein the viral antigen is an influenza virus antigen.

4. The immunogenic complex according to claim 2, wherein the viral antigen is a foot and mouth disease virus antigen.

5. The immunogenic complex according to claim 4, wherein the MHC antigen is bovine or porcine LA.

6. The immunogenic complex according to claim 1, wherein the MHC antigen is an HLA antigen or an HLA-analogous MHC antigen of a non-human animal species.

7. The immunogenic complex according to claim 1, wherein the second antigen is bonded to the MHC antigen through hydrogen bonding, ionic bonding, hydrophobic bonding or covalent bonding.

8. A synthetic immunogenic complex comprising a purified MHC antigen bonded to a second antigen selected from the group consisting of bacterial antigens and hormone peptide antigens.

9. The immunogenic complex according to claim 8, wherein the second antigen is a bacterial antigen.

10. The immunogenic complex according to claim 9, wherein the bacterial antigen is a bacterial toxin or toxoid.

11. The immunogenic complex according to claim 10, wherein the toxoid is diptheria toxoid.

12. The immunogenic complex according to claim 8, wherein the second antigen is a hormone peptide.

13. The immunogenic complex according to claim 12, wherein the hormone peptide is HCG.

14. A synthetic immunogenic complex comprising a purified MHC-protein complex, wherein an MHC antigen is complexed with a protein with which said MHC antigen is normally associated in nature, said MHC-protein complex being bonded to a second antigen through either the protein portion or the MHC portion of the MHC-protein complex.

15. The immunogenic complex according to claim 14, wherein the second antigen is a bacterial antigen.

16. The immunogenic complex according to claim 15, wherein the bacterial antigen is a bacterial toxin or toxoid.

17. The immunogenic complex according to claim 16, wherein the toxoid is diptheria toxoid.

18. The immunogenic complex according to claim 14, wherein the second antigen is a viral antigen.

19. The immunogenic complex according to claim 18, wherein the viral antigen is an influenza virus antigen.

20. The immunogenic complex according to claim 18, wherein the viral antigen is a foot and mouth disease virus antigen.

21. The immunogenic complex according to claim 20, wherein the MHC antigen is bovine or porcine LA.

22. The immunogenic complex according to claim 14, wherein the second antigen is a hormone peptide.

23. The immunogenic complex according to claim 22, wherein the hormone peptide is HCG.

24. The immunogenic complex according to claim 14, wherein the MHC antigen is an HLA antigen or an HLA-analogous MHC antigen of a non-human animal species.

25. The immunogenic complex according to claim 14, wherein the second antigen is covalently attached to the protein portion of the MHC-protein complex.

26. The immunogenic complex according to claim 14, wherein the second antigen is attached to the protein portion of the MHC-protein complex through a linking group.

27. The immunogenic complex according to claim 26, wherein the linking group is derived from a heterobifunctional coupler.

28. The immunogenic complex according to claim 27, wherein the heterobifunctional coupler is m-maleimidobenzoyl-N-hydroxysuccinimide ester.

29. An immunogenic composition, comprising:
an immunogenically effective amount of a synthetic immunogenic complex comprising a purified MHC antigen or a purified MHC-protein complex, wherein an MHC antigen is complexed with a protein with which said MHC antigen is normally associated in nature, said MHC antigen or MHC-protein complex being bonded to a second antigen; and
a pharmaceutically acceptable diluent.

30. The immunogenic composition according to claim 29, wherein said MHC antigen or MHC-protein complex is a purified MHC-protein complex and said second antigen is bonded to said MHC-protein complex through either the protein portion or the MHC portion of the MHC-protein complex.

31. The immunogenic composition according to claim 30, wherein said bonding is through said protein portion.

32. The immunogenic composition according to claim 31, wherein the second antigen is bonded to the protein portion of the MHC-protein complex through a linking group.

33. The immunogenic composition according to claim 32, wherein the linking group is derived from a heterobifunctional coupler.

34. The immunogenic composition according to claim 33, wherein the heterobifunctional coupler is m-maleimidobenzoyl-N-hydroxysuccinimide ester.

35. The immunogenic composition according to claim 29, wherein the MHC-protein complex is HLA-B2M.

36. The immunogenic composition according to claim 29, wherein the second antigen is a bacterial antigen.

37. The immunogenic composition according to claim 36, wherein the bacterial antigen is a bacterial toxin or toxoid.

38. The immunogenic composition according to claim 29, wherein the second antigen is a viral antigen.

39. The immunogenic composition according to claim 38, wherein the viral antigen is an influenza virus antigen.

40. The immunogenic composition according to claim 34, wherein the second antigen is a hormone peptide.

41. The immunogenic composition according to claim 40, wherein the hormone peptide is HCG.

42. A method for the production of an immunogenic response in an animal which comprises administering to said animal an immunogenically effective amount of a synthetic immunogenic complex comprising a purified MHC antigen or a purified MHC-protein complex, wherein an MHC antigen is complexed with a protein with which said MHC antigen is normally associated in nature, said MHC antigen or MHC-protein complex being bonded to a second antigen.

43. The method according to claim 42, wherein said MHC antigen or MHC-protein complex is a purified MHC-protein complex and said second antigen is bonded to said MHC-protein complex through either the protein portion or the MHC portion of the MHC-protein complex.

44. The method according to claim 43, wherein the MHC-protein complex is HLA-B2M.

45. The method according to claim 43, wherein the second antigen is attached to the protein portion of the MHC-protein complex through a linking group.

46. The method according to claim 45, wherein the linking group is derived from a heterobifunctional coupler.

47. The method according to claim 46, wherein the heterbifunctional coupler is m-maleimidobenzoyl-N-hydroxysuccinimide ester.

48. The method according to claim 42, wherein the second antigen is a bacterial antigen.

49. The method according to claim 48, wherein the bacterial antigen is a bacterial toxin or toxoid.

* * * * *